US010172927B2

(12) United States Patent
Akira et al.

(10) Patent No.: US 10,172,927 B2
(45) Date of Patent: *Jan. 8, 2019

(54) DETECTION/MEASUREMENT OF MALARIA INFECTION DISEASE UTILIZING NATURAL IMMUNITY BY HEMOZOIN INDUCTION, SCREENING OF PREVENTATIVE OR THERAPEUTIC MEDICINE FOR MALARIA INFECTION DISEASE, AND REGULATION OF NATURAL IMMUNITY INDUCTION

(71) Applicant: Osaka University, Osaka (JP)

(72) Inventors: Shizuo Akira, Osaka (JP); Ken Ishii, Osaka (JP); Cevayir Coban, Osaka (JP)

(73) Assignee: Osaka University, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/189,234

(22) Filed: Jun. 22, 2016

(65) Prior Publication Data

US 2016/0296613 A1 Oct. 13, 2016

Related U.S. Application Data

(62) Division of application No. 13/312,260, filed on Dec. 6, 2011, now Pat. No. 9,400,279, which is a division of application No. 11/792,668, filed as application No. PCT/JP2005/020283 on Nov. 4, 2005.

(30) Foreign Application Priority Data

Dec. 9, 2004 (JP) ................................. 2004-357255

(51) Int. Cl.
*A61K 39/015* (2006.01)
*G01N 33/569* (2006.01)
*A61K 39/00* (2006.01)

(52) U.S. Cl.
CPC ..... *A61K 39/015* (2013.01); *G01N 33/56905* (2013.01); *A01K 2267/0387* (2013.01); *A61K 2039/572* (2013.01); *G01N 2333/445* (2013.01); *G01N 2333/70596* (2013.01); *G01N 2500/10* (2013.01)

(58) Field of Classification Search
None
See application file for complete search history.

(56) References Cited

U.S. PATENT DOCUMENTS 5,849,307 A 12/1998 Metz et al.
2004/0053843 A1 3/2004 Bucala et al.

FOREIGN PATENT DOCUMENTS

| JP | 2002-034565 | 5/2002 |
| WO | WO 92/14149 A1 | 8/1992 |
| WO | WO 01/55386 A1 | 8/2001 |

OTHER PUBLICATIONS

Adachi et al., "*Plasmodium berghei* Infection in Mice Induces Liver Injury by an IL-12- and Toll-Like Receptor/Myeloid Differentiation Factor 88-Dependent Mechanism," The Journal of Immunology, 2001, 167:5928-5934.
Akira et al., "Toll-Like Receptor Signalling," Nature Reviews: Immunology, Jul. 2004, 4:499-511.
Arese et al., "Proceedings of a Malaria Meeting of the British Society for Parasitology, Malarial pigment (haemozoin): a very active 'inert' substance," Ann. Trop. Med. Parasitol., 1997, 91:501-516, Abstract only.
Ba et al., "Malaria-specific metabolite homozoin mediates the release of several potent endogenous pyrogens (TNF, MIP-1 alpha, and MIP-1 beta) in vitro, and altered thermoregulation in vivo," J. Inflamm., 1995, 45(2):85-96, Abstract only.
Janeway et al., "Innate Immune Recognition," Ann. Rev. Immunol., 2002, 20:197-216.
Kwiatkowski et al., "The malarial fever response—pathogenesis, polymorphism and prospects for intervention," Ann. Trop. Med. Parasitol., 1997, 91:533-542, Abstract only.
Miller et al., "Research toward vaccines against malaria," Nature Medicine Vaccine Supplement, May 1998, 4(5):520-524.
Stevenson et al., "Innate Immunity to Malaria," Nature Reviews: Immunology, Mar. 2004, 4:169-180.
Sullivan et al., "Theories on malarial pigment formation and quinolone action," International Journal of Parasitology, Dec. 4, 2002, 32(13):1645-1653, Abstract only.
Bauer et al., "Human TLR9 confers responsiveness to bacterial DNA via species-specific CpG motif recognition," PNAS, Jul. 31, 2001, 98(16):9237-9242.
Bowie et al., "Deciphering the Message in Protein Sequences: Tolerance to Amino Acid Substitutions," Science, Mar. 16, 1990, 257:1306-1310.
Coban et al., "Purified Malaria Pigment (Hemozoin) Enhances Dendritic Cell Maturation and Modulates the Isotype of Antibodies Indeuced by a DNA Vaccine," Infection and Immunity, Jul. 2002, 70(7):3939-3943.
Coban et al., "Toll-like receptor 9 mediates innate immune activation by the malaria pigment hemozoin," JEM, Jan. 3, 2005, 201(1):19-25.

(Continued)

*Primary Examiner* — Robert A Zeman
(74) *Attorney, Agent, or Firm* — Foley & Lardner LLP

(57) ABSTRACT

The instant invention is to provide a method for detecting and measuring malaria infection utilizing the induction by hemozoin (HZ); a method for screening a vaccine for malaria infection and a preventative or therapeutic agent for malaria infection using the method for detecting and measuring; and a means for regulating the induction of innate immunity using the HZ, synthetic HZ, or derivatives thereof as an adjuvant or immunostimulant. Malaria infection is detected and measured of by detecting and measuring HZ-induced, TLR9-mediated, and MyD88-dependent innate immune activity. The detection and measurement of malaria infection can be used to diagnose malaria infection. The method for detecting and measuring is also used for screening a vaccine for malaria infection and a preventative or therapeutic agent for malaria infection. Further, HZ, synthetic HZ, or derivatives thereof are used as an adjuvant or immunostimulant to regulate HZ-induced innate immune induction.

3 Claims, 8 Drawing Sheets

Specification includes a Sequence Listing.

(56) References Cited

OTHER PUBLICATIONS

Coban et al., "Toll-Like Receptor 9 Recognizes Malaria Pigment Hemozoin," The Japanese Society for Immunology Gakujutsu Shukai Kiroku, Nov. 5, 2004, 34:175, 2-D-W23-17-O/P.
Hong et al., "Chloroquine protects mice from challenge with CpG ODN and LPS by decreasing proinflammatory cytokine release," International Immunopharmacology, Feb. 2004, 4:223-234.
Lindblad, "Aluminum compounds for use in vaccines," Immunology and Cell Biology, 2004, 82:497-505.
Pagola et al., "The structure of malaria pigment β-haematin," Nature, Mar. 16, 2000, 404:307-310.
Pichyangkul et al., "Malaria Blood Stage Parasites Activate Human Plasmacytoid Dendritic Cells and Murine Dendritic Cells through a Toll-Like Receptor 9-Dependent Pathway," Journal of Immunology, Apr. 2004, 172:4926-4933.
Rhodes, J., "Discovery of immunopotentiatory drugs: current and future strategies," Clin. Exp. Immunol., 2002, 130:363-369.

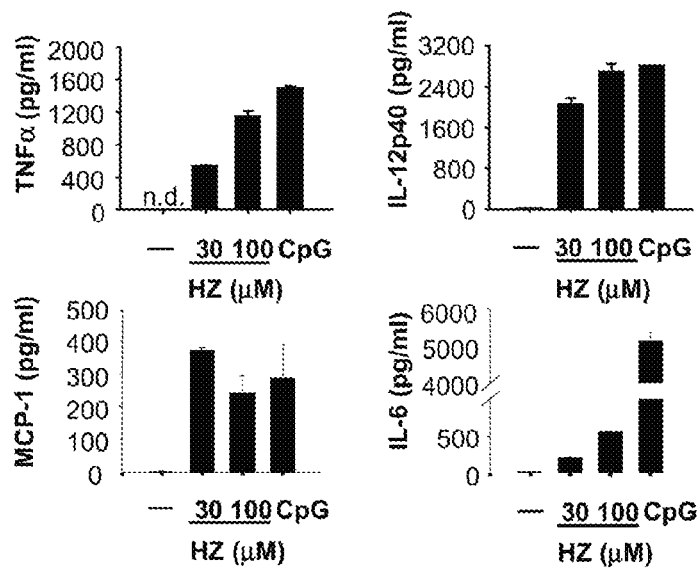
[Fig.1a]
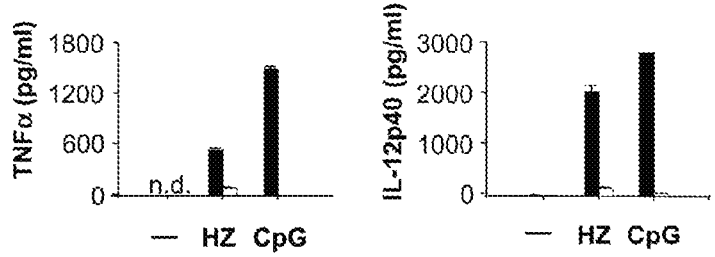
[Fig.1b]
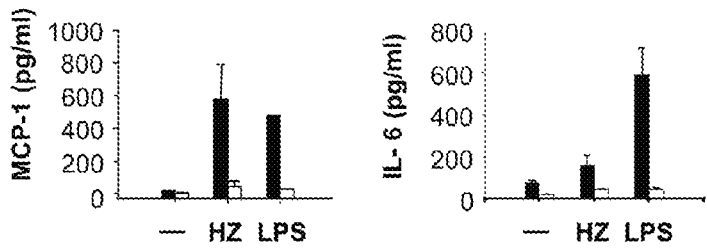
[Fig.1c]

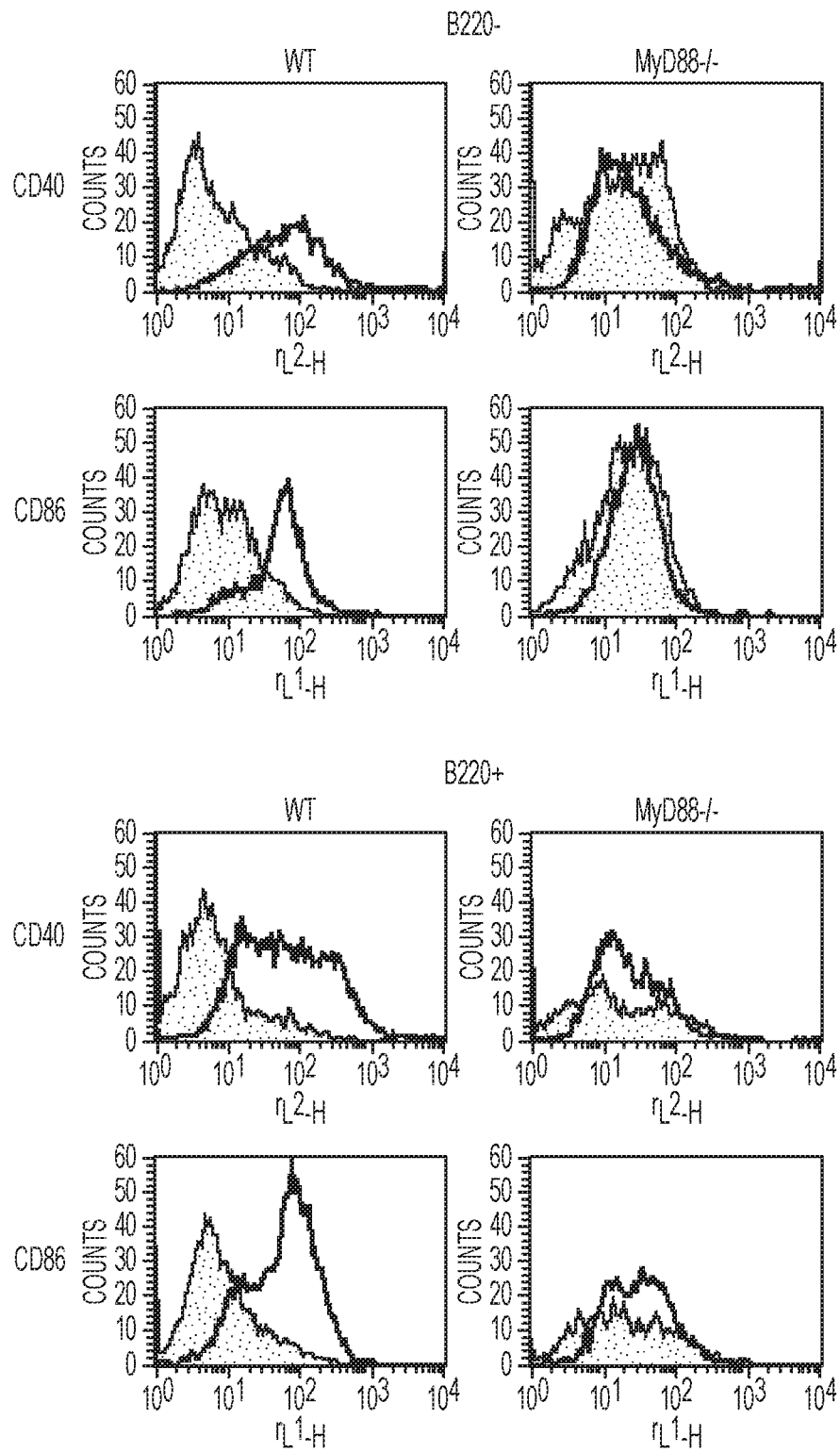
[Fig.1d]

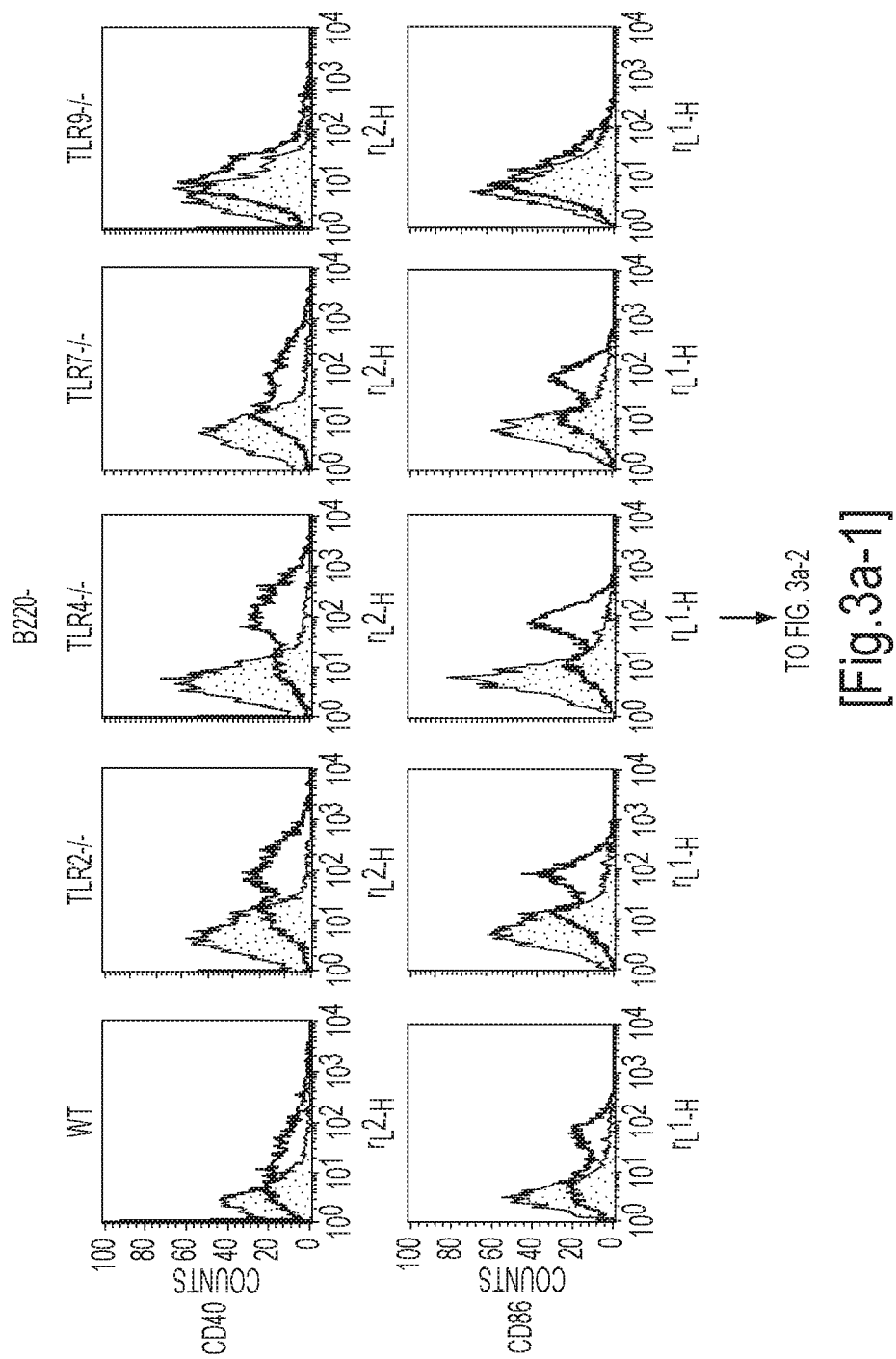

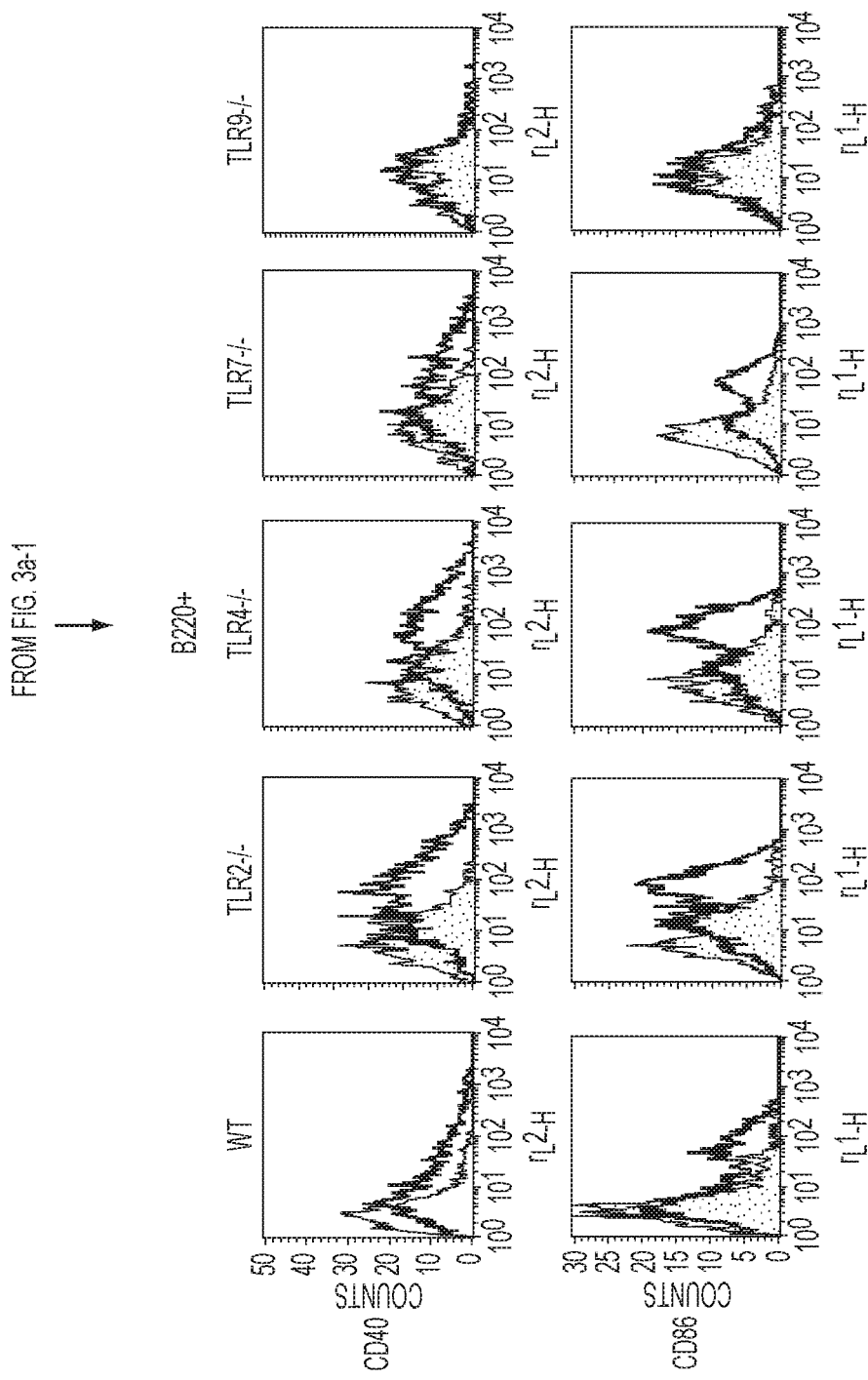
[Fig.3a-2]

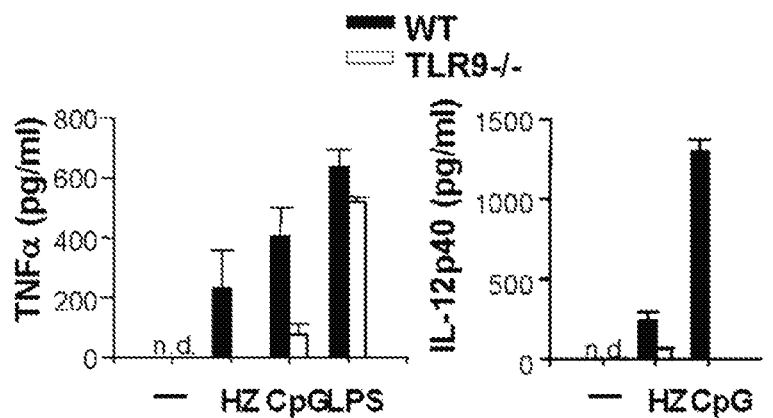
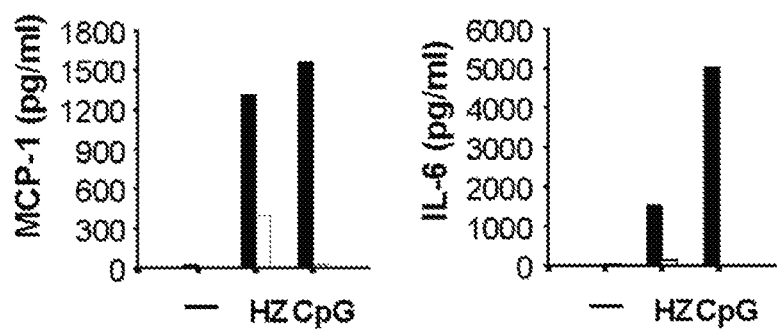
[Fig.3b]
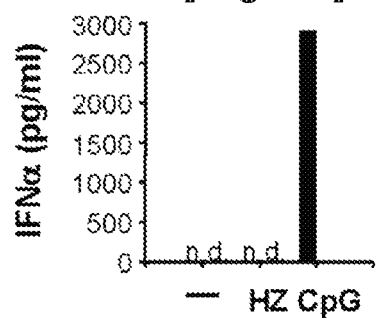
[Fig.3c]

Fig. 5a
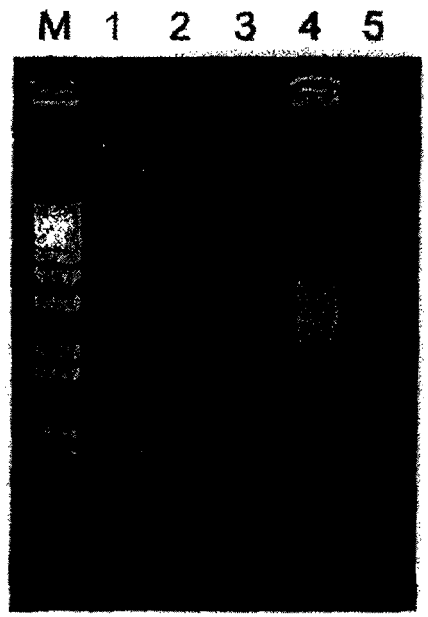
Fig. 5b
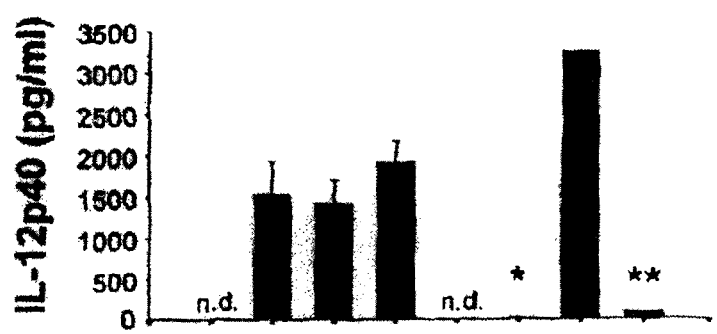
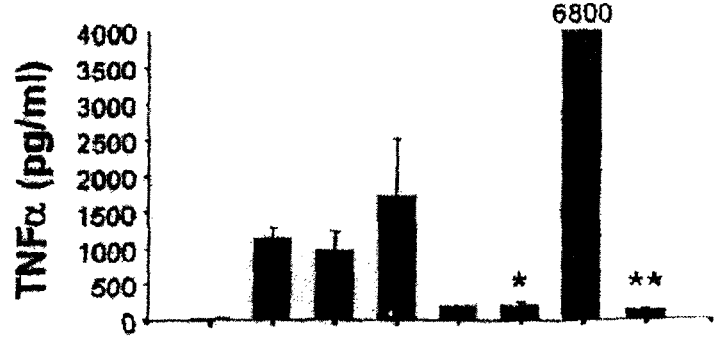
| | | | | | | | | |
|---|---|---|---|---|---|---|---|---|
| HZ | − | + | + | + | − | + | − | − |
| DNase | − | − | + | − | − | − | − | − |
| Heat In. | − | − | − | + | − | − | − | − |
| CQ | − | − | − | − | + | + | − | + |
| CpG | − | − | − | − | − | − | + | + |

DETECTION/MEASUREMENT OF MALARIA INFECTION DISEASE UTILIZING NATURAL IMMUNITY BY HEMOZOIN INDUCTION, SCREENING OF PREVENTATIVE OR THERAPEUTIC MEDICINE FOR MALARIA INFECTION DISEASE, AND REGULATION OF NATURAL IMMUNITY INDUCTION

CROSS-REFERENCE TO RELATED PATENT APPLICATIONS

This application is a Divisional of U.S. application Ser. No. 13/312,260, now U.S. Pat. No. 9,400,279, filed Dec. 6, 2011, which is a Divisional of U.S. application Ser. No. 11/792,668, now abandoned, which is the US National Stage application of PCT/JP2005/020283, filed Nov. 4, 2005, which claims priority from Japanese application JP 2004-357255, filed Dec. 9, 2004, the entire contents of which are incorporated by reference herein.

The instant application contains a Sequence Listing which has been submitted in ASCII format via EFS-WEB and is hereby incorporated by reference in its entirety. Said ASCII copy, created on May 18, 2016, is named sequence.txt and is 14 KB.

BACKGROUND OF THE INVENTION

Technical Field

The instant invention relates to a method for detecting and measuring malaria infection by detecting and measuring TLR9-mediated, MyD88-dependent innate immune activity induced by hemozoin, hydrophobic heme polymers produced as a hemoglobin metabolite by malaria parasites; screening of a vaccine for malaria infection or a preventative or therapeutic agent for malaria infection using the method for detection and measurement; regulation of the induction of innate immunity using the hemozoin or synthetic hemozoin as an adjuvant or immunostimulant; a TLR9 agonist containing hemozoin, synthetic hemozoin or derivatives thereof as an active ingredient; and the like.

Background Art

Malaria infection is the major cause of disease and mortality of humans, especially in the tropical regions of the world. Due to a complex life cycle and rapid polymorphism of malaria parasites, host-parasite interactions and resulting innate immune responses to malaria parasites are still poorly understood despite the necessity of effective immunotherapies against malaria (Nat. Med. 4: 520-524, 1998; Nat. Rev. Immunol. 4: 169-180, 2004). Robust innate immune activation, including proinflammatory cytokine production in response to malaria parasites and/or a metabolite released from ruptured infected red blood cells, has been linked to the major symptoms such as high fever (Ann. Trop. Med. Parasitol. 91: 533-542, 1997). Recent evidence suggests that toll-like receptors (TLRs) are involved in innate immune responses to a variety of pathogens including Plasmodium (Annu. Rev. Immunol. 20: 197-216, 2002; Nat. Rev. Immunol. 4: 499-511, 2004).

In murine malaria infection, myeloid differentiation factor 88 (MyD88), an essential adaptor molecule for TLR-mediated cytokine production, was shown to be critical for IL-12 induction by Plasmodium berghei parasites that cause liver damage (J. Immunol. 167: 5928-5934, 2001). A recent study has reported that *P. falciparum* blood-stage parasites activate human plasmacytoid dendritic cells (DCs) and murine DCs through MyD88-dependent and TLR9-dependent pathways. Although the responsible molecule is yet unidentified, it is suggested that the molecule is a protein contained in schizont lysate or a complex thereof (J. Immunol. 172: 4926-4933, 2004).

Hemozoin (HZ), known as a malaria pigment, is a detoxification product of heme molecules persisting in food vacuoles of Plasmodium parasites (Int. J. Parasitol. 32: 1645-1653, 2002; Ann. Trop. Med. Parasitol. 91: 501-516, 1997). Intercellular HZ is released into blood during schizont rupture and phagocytosed by myeloid cells, which results in the concentration of HZ in the reticulo-endothelial system (Ann. Trop. Med. Parasitol. 91: 501-516, 1997). Specifically, malaria parasites in the red blood cells digest host hemoglobin to hydrophobic heme polymers known as HZ. Then the polymers are released into the blood stream, captured in the reticulo-endotherial system, and accumulate in the system. It has been reported that HZ produced from *P. falciparum* activates macrophages to produce proinflammatory cytokines, chemokines and nitrogen, and enhances the maturation of human myeloid dendritic cells (DCs) (J. Inflamm. 45: 85-96, 1995; Infect. Immun. 70: 3939-3943, 2002). These studies promoted the need for studying the molecular mechanism through which HZ activates innate immunity and for better understanding the malaria parasite-host interactions.

Non-patent document 1: Nat. Med. 4: 520-524, 1998
Non-patent document 2: Nat. Rev. Immunol. 4: 169-180, 2004
Non-patent document 3: Ann. Trop. Med. Parasitol. 91: 533-542, 1997
Non-patent document 4: Annu. Rev. Immunol. 20: 197-216, 2002
Non-patent document 5: Nat. Rev. Immunol. 4: 499-511, 2004
Non-patent document 6: J. Immunol. 167: 5928-5934, 2001
Non-patent document 7: J. Immunol. 172: 4926-4933, 2004
Non-patent document 8: Int. J. Parasitol. 32: 1645-1653, 2002
Non-patent document 9: Ann. Trop. Med. Parasitol. 91: 501-516, 1997
Non-patent document 10: J. Inflamm. 45: 85-96, 1995
Non-patent document 11: Infect. Immun. 70: 3939-3943, 2002

DISCLOSURE OF THE INVENTION

Object to be Solved by the Invention

An object of the instant invention is to elucidate the malaria parasite-host interactions in malaria infection, and to provide, based on the findings, a method for detecting and measuring malaria infection utilizing an induction by hemozoin (HZ), hydrophobic heme polymers produced as a hemoglobin metabolite by malaria parasites, for the diagnosis of malaria infection; screening of a vaccine for malaria infection and of a preventative or therapeutic agent for malaria infection using the method for detection and measurement; and a means for regulating the induction of innate immunity using the HZ, synthetic HZ or derivatives thereof as an adjuvant or immunostimulant; and the like.

MEANS TO SOLVE THE OBJECT

Malaria parasites in red blood cells digest host hemoglobin to hydrophobic heme polymers known as hemozoin (HZ). The polymers are then released into the blood stream, captured in the reticulo-endothelial system and accumulated in the system. While studying about malaria parasite-host interactions to elucidate the molecular-level mechanism of the immune responses in which HZ activates innate immunity, the present inventors found that HZ, the heme metabolite produced by human *falciparum* malaria parasites, is a novel ligand that strongly stimulates toll-like receptor 9 (TLR9), a receptor for innate immunity. More specifically, the present inventors found that HZ purified from *P. falciparum* activates MyD88-dependent murine immune cells through TLR9 both in vitro and in vivo, and confirmed that this activation is inhibited by chloroquine, a known antimalarial agent.

Based on these findings, the present inventors found that it is possible to detect and measure malaria infection by detecting and measuring the HZ-induced, TLR9-mediated, and MyD88-dependent innate immune activity, and that the detection and measurement of malaria infection can be used for the diagnosis of malaria infection, and thus the instant invention has been completed. The present inventors also found that it is possible to screen a vaccine for malaria infection or of a preventative or therapeutic agent for malaria infection using the method for detecting and measuring malaria infection by detecting and measuring the HZ-induced innate immune activity, and thus the instant invention has been accomplished. Further, based on the above findings, the present inventors found that it is possible to regulate HZ-induced, TLR-9 mediated, and MyD88-dependent innate immune induction using HZ, synthetic HZ, or derivatives thereof as an adjuvant or immunostimulant. Specifically, the present inventors became the first to demonstrate that hemozoin is a ligand with a selective immune-response control and activation effect which induces Th1 via TLR9-MyD88 dependent pathway but does not activate other TLR families or TRIF dependent pathway which is a MyD88-independent pathway. The instant invention has been accomplished as a result of the above findings.

More specifically, the instant invention relates to a method for detecting and measuring malaria infection, wherein a TLR9-mediated, MyD88-dependend innate immune activity induced by hemozoin that is hydrophobic heme polymers produced as a hemoglobin metabolite by malaria parasites, is detected and measured ("1"); the method for detecting and measuring malaria infection according to "1", wherein the detection and measurement of an innate immune activity is a detection and measurement of an immune-cell activation ("2"); the method for detecting and measuring malaria infection according to "2", wherein the detection and measurement of an immune-cell activation is a detection and measurement of a cytokine production by immune cells ("3"); the method for detecting and measuring malaria infection according to "3", wherein the cytokine is one or more cytokines selected from TNF-α, IL-12p40, MCP-1, IL-6, and IFNα ("4"); the method for detecting and measuring malaria infection according to any one of "2" to "4", wherein the immune-cell is a spleen-cell or dendritic-cell ("5"); a method for screening or testing the quality of a vaccine for malaria infection, wherein a method for detecting and measuring malaria infection according to any one of "1" to "5" is used as a method for evaluating a test vaccine ("6"); a method for screening a preventative or therapeutic agent for malaria infection, wherein a TLR9-mediated, MyD88-dependent innate immune activity induced by hemozoin that is hydrophobic heme polymers produced as a hemoglobin metabolite by malaria parasites, synthetic hemozoin, or derivatives thereof, is detected and measured in the presence of a test substance ("7"); and a method for screening a preventative or therapeutic agent for malaria infection, wherein a method for detecting and measuring an innate immune activity is a method for detecting and measuring an innate immune activity according to any one of "2" to "5" ("8").

The instant invention is also comprised of an adjuvant for regulating an induction of TLR9-mediated, MyD88-dependent innate immunity, which consists of hemozoin that is hydrophobic heme polymers produced as a hemoglobin metabolite by malaria parasites, synthetic hemozoin, or derivatives thereof ("9"); and an immunostimulant for inducing TLR9-mediated, MyD88-dependent innate immunity, comprising as an active ingredient hemozoin that is hydrophobic heme polymers produced as a hemoglobin metabolite by malaria parasites, synthetic hemozoin, or derivatives thereof ("10").

The instant invention further relates to a method for screening a preventative or therapeutic agent for malaria infection, wherein a cytokine production level in the case of administering a test substance and hemozoin, synthetic hemozoin, or derivatives thereof to MyD88+/+ and TLR9+/+ nonhuman animal and a cytokine production level in the case of administering a test substance and hemozoin, synthetic hemozoin, or derivatives thereof to MyD88−/− and/or TLR9−/− nonhuman animal, are measured and evaluated ("11"); the method for screening a preventative or therapeutic agent for malaria infection according to "11", wherein the cytokine production level is measured as a serum cytokine level by ELISA ("12"); the method for screening according to "11" or "12", wherein the nonhuman animal is a mouse ("13"); a method for screening a preventative or therapeutic agent for malaria infection, wherein a cytokine production level in cells in the case of administering a test substance and hemozoin, synthetic hemozoin, or derivatives thereof to MyD88+/+ and TLR9+/+ gene-expressing cells and a cytokine production level in cells in the case of administering a test substance and hemozoin, synthetic hemozoin, or derivatives thereof to MyD88−/− and/or TLR9−/− gene-expressing cells, are compared and evaluated ("14"); the method for screening a preventative or therapeutic agent for malaria infection according to "14", wherein the cells are spleen cells or dendritic cells ("15"); the method for screening a preventative or therapeutic agent for malaria infection according to "14" or "15", wherein the cytokine production level in cells is measured as a cytokine level in a cell-culture supernatant by ELISA ("16"); and the method for screening a preventative or therapeutic agent for malaria infection according to any one of "11" to "16", wherein the measurement of the cytokine production level is a measurement of the production of any one or more cytokines selected from TNF-α, IL-12p40, MCP-1, IL-6, and IFNα ("17").

The instant invention furthermore relates to a method for using protein (a) or (b) as defined below as a receptor for a ligand consisting of hemozoin, synthetic hemozoin, or derivatives thereof: (a) a protein consisting of the amino acid sequence shown by SEQ ID No: 2; (b) a protein consisting of an amino acid sequence in which one or a few amino acids are deleted, substituted, or added in the amino acid sequence shown by SEQ ID No: 2, the protein being responsive to hemozoin, synthetic hemozoin, or derivatives thereof ("18"); the method for using according to "18", wherein the protein is encoded by a DNA comprising the nucleotide sequence shown by SEQ ID No: 1 or a complementary sequence thereof ("19"); the method for using according to "18", wherein the protein is encoded by a DNA which hybridizes under a stringent condition with a DNA comprising the nucleotide sequence shown by SEQ ID No: 1 or a complementary sequence thereof ("20"); a method for using hemozoin, synthetic hemozoin, or derivatives thereof as a ligand for receptor protein (a) or (b) as defined below: (a) a protein consisting of the amino acid sequence shown by SEQ ID No: 2; (b) a protein consisting of an amino acid sequence in which one or a few amino acids are deleted, substituted, or added in the amino acid sequence shown by SEQ ID No: 2, the protein being responsive to hemozoin, synthetic hemozoin, or derivatives thereof ("21"); the method for using according to "21", wherein the protein is encoded by a DNA comprising the nucleotide sequence shown by SEQ ID No: 1 or a complementary sequence thereof ("22"); and the method for using according to "21", wherein the protein is encoded by a DNA which hybridizes under a stringent condition with a DNA comprising the nucleotide sequence shown by SEQ ID No: 1 or a complementary sequence thereof, the protein being responsive to hemozoin ("23").

The instant invention still further relates to a TLR9 agonist which contains hemozoin, synthetic hemozoin, or derivatives thereof as an active ingredient ("24"); the TLR9 agonist according to "24", which activates MyD88 ("25"); the TLR9 agonist according to "25", which induces an immune response through the TLR-MyD88-dependent pathway ("26"); the TLR9 agonist according to "26", wherein the immune response through the TLR-MyD88-dependent pathway is a production of any one or more cytokines selected from TNF-α, IL-12p40, MCP-1, IL-6, and IFNα ("27"); the TLR9 agonist according to any one of "24" to "27", which activates TLR9 selectively ("28"); the TLR9 agonist according to "28", which does not activate TLR2, TLR4, TLR7, or TRIF ("29"); and the TLR9 agonist according to any one of "24" to "29", which is used as an agent for controlling innate immunity ("30").

The instant invention furthermore relates to a method for using hemozoin, synthetic hemozoin, or derivatives thereof as a ligand for TLR9 ("31"), the method for using according to "31", which comprises a method for inducing an immune response through the TLR9-MyD88-dependent pathway ("32"); the method for using according to "32", wherein the immune response through the TLR9-MyD88-dependent pathway is a production of any one or more cytokines selected from TNF-α, IL-12p40, MCP-1, IL-6, and IFNα ("33"); and the method for using according to any one of "31" to "33", which comprises a method for controlling innate immunity ("34").

BRIEF DESCRIPTION OF DRAWINGS

FIGS. 1a to 1d are a series of figures showing the results of the measurement of proinflammatory cytokine productions in the culture supernatant by ELISA after stimulating spleen cells and DCs (human myeloid dendritic cells) with purified HZ in vitro, to study whether purified HZ from P. falciparum activates the murine immune system in an example of the instant invention.

FIGS. 3a-1 to 3c are a series of figures showing (b) the results of flow cytometric analysis for CD40 and CD86 expressions and (c) the results of ELISA analysis for IFNα production by FL-DCs, using spleen cells and DCs to study whether HZ-induced innate immune activation is impaired or altered in an example of the instant invention.

FIGS. 5a to 5b are a set of figures showing the results of the analysis to determine the purity of HZ to exclude any possible contaminants in P. falciparum culture or during HZ preparation from P. falciparum culture, in an example of the instant invention. (a) shows the results of ethidium-bromide staining of HZ that was run on an agarose gel for the detection of DNA contamination and (b) shows the results of the measurement of TNFα and IL-12p40 by ELISA after FL-DCs from C57/B6 mice were incubated with either HZ or DNase treatment, heat-inactivation, and/or CQ (10μM).

BEST MODE OF CARRYING OUT THE INVENTION

Figure 2:
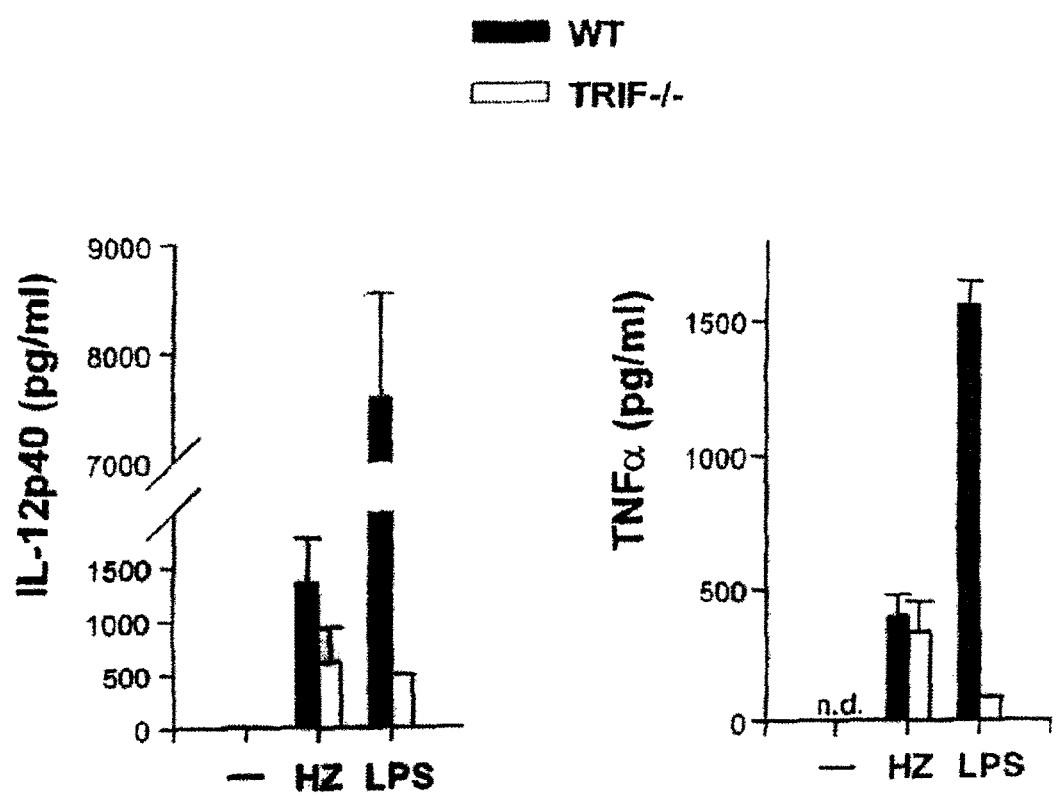
FIG. 2 is a set of figures showing the results of the analysis and determination of TNFα or IL-12p40 production level by ELISA using mice lacking TRIF (Toll/IL-1 receptor (TIR)-region-containing adaptor), an essential adaptor molecule for the MyD88-independent pathway, to confirm that HZ-induced innate immune activation is solely dependent on MyD88 in an example of the instant invention.

The instant invention is comprised of a method wherein malaria infection is detected and measured by detecting and measuring TLR9-mediated, MyD88-dependent innate immune activity induced by HZ, hydrophobic heme polymers produced as a hemoglobin metabolite by malaria parasites. In the instant invention, HZ-induced innate immune activity can be detected and measured by detecting and measuring the state of TLR9-mediated, MyD88-dependent activation by HZ in immune cells such as spleen cells or dendritic cells. TLR9-mediated, MyD88-dependent activation by HZ can be detected and measured by detecting and measuring HZ-induced cytokine productions in immune cells. Cytokine production can be detected and measured by detecting and measuring the production of any one or more cytokines selected from TNF-α, IL-12p40, MCP-1, IL-6, and IFNα. Common cytokine detection and measurement methods such as cytokine ELISA method can be used for the detection and measurement of the cytokine production. The diagnosis of malaria infection is enabled by the method for detecting and measuring malaria infection of the instant invention.

The instant invention is further comprised of using the method for detecting and measuring malaria infection by HZ induction of the instant invention as a method for evaluating a test vaccine thus as a method for screening or testing a vaccine for malaria infection. The method for screening or testing a vaccine can be used as a method for evaluating test vaccines in developing a vaccine, in tests involved in the manufacture of the developed vaccine, and the like. The instant invention is furthermore comprised of using the method for detecting and measuring malaria infection of the instant invention as a method for screening a preventative or therapeutic agent for malaria infection. The method for screening can be performed by the method of the instant invention wherein TLR9-mediated, MyD88-dependent innate immune activity induced by HZ, synthetic HZ, or derivatives thereof is detected and measured in the presence of a test substance.

The instant invention is still further comprised of using HZ, synthetic HZ, or derivatives thereof that has been found out to be a novel ligand for TLR9 in the instant invention, as an adjuvant for regulating the induction of innate immunity or as an immunostimulant for inducing innate immunity. An induction of TLR9-mediated, MyD88-dependent innate immunity can be regulated by using HZ, synthetic HZ, or derivatives thereof as an adjuvant for regulating the induction of innate immunity or as an immunostimulant for inducing innate immunity. In the instant invention, HZ (insoluble crystalloid structure) can be prepared by the method for purifying from red blood cells that are infected with *P. falciparum* (3D7 strain) (Infect. Immun. 70: 3939-3943, 2002: Proc. Natl. Acad. Sci. U.S.A 93: 11865-11870, 1996; Proc. Natl. Acad. Sci. U.S.A 88: 325-329, 1991). Further, synthetic HZ (β-hematin) can be manufactured by the purification employing the protocol of Jaramillo et al. (J. Immunol. 172: 3101-3110) based on acetic acid treatment and alkaline bicarbonate wash. Both the adjuvant for regulating the induction of innate immunity and the immunostimulant for inducing innate immunity can be applied according to commonly known application forms.

The instant invention further relates to a method for screening a preventative or therapeutic agent for malaria infection, wherein the cytokine production level in the case of administering a test substance and hemozoin, synthetic hemozoin or derivatives thereof to MyD88+/+ and TLR9+/+ nonhuman animals such as wild type mice, and the cytokine production level in the case of administering a test substance and hemozoin, synthetic hemozoin or derivatives thereof to MyD88−/− and/or TLR9−/− nonhuman animal, are measured and evaluated; and a method for screening a preventative or therapeutic agent for malaria infection, wherein the cytokine production level in cells in the case of administering a test substance and hemozoin, synthetic hemozoin, or derivatives thereof to MyD88+/+ and TLR9+/+ gene-expressing cells such as spleen cells, dendritic cells and the like, and the cytokine production level in the case of administering a test substance and hemozoin, synthetic hemozoin, or derivatives thereof to MyD88−/− and/or TLR9−/− gene-expressing cells, are compared and evaluated. The above cytokines can be exemplified by TNF-α, IL-12p40, MCP-1, IL-6, IFNα. Further, the cytokine production level in the above nonhuman animals can be measured as a serum cytokine level in the nonhuman animals by ELISA, and the cytokine production level in cells can be measured as the cytokine level in the cell-culture supernatant by ELISA. Further, MyD88−/− mice and MyD88−/− gene-expressing cells can be prepared by the method described in the publication of WO00/41561, and TLR9−/− mice and TLR9−/− gene-expressing cells by the method described in Japanese Laid-Open Patent Application No. 2002-34565.

The instant invention furthermore relates to a method for using (a) a protein consisting of the amino acid sequence shown by SEQ ID No: 2; or (b) a protein consisting of an amino acid sequence in which one or a few amino acids are deleted, substituted, or added in the amino acid sequence shown by SEQ ID No: 2, and is responsive to hemozoin, synthetic hemozoin, or derivatives thereof, as a receptor for a ligand consisting of hemozoin, synthetic hemozoin, or derivatives thereof. As above proteins, a protein encoded by a DNA comprising the nucleotide sequence shown by SEQ ID No: 1 or a complementary sequence thereof; or a protein encoded by a DNA which hybridizes under a stringent condition with a DNA comprising the nucleotide sequence shown by SEQ ID No: 1 or a complementary sequence thereof, and is responsive to hemozoin, synthetic hemozoin, or derivatives thereof, can be used. Herein, "under a stringent condition" means a condition under which so-called specific hybrids are formed and nonspecific hybrids are not formed. More specifically, such conditions include a condition wherein DNAs with 50-70% or more homology are hybridized and DNAs with less homology are not hybridized, or a hybridization condition with a salt concentration corresponding to 1×SSC, 0.1% SDS or 0.1×SSC, 0.1% SDS at 65° C., which is an usual washing condition in southern hybridization.

Specific aspects of the above method for using the instant invention include: a method for detecting and measuring malaria infection, wherein TLR9-mediated, MyD88-dependent innate immune activity induced by hemozoin, synthetic hemozoin, or derivatives thereof is detected and measured; a method for screening or testing the quality of a vaccine for malaria infection; a method for screening a preventative or therapeutic agent for malaria infection, wherein TLR9-mediated, MyD88-dependent innate immune activity induced by hemozoin, synthetic hemozoin, or derivatives thereof is detected and measured; a method for screening a preventative or therapeutic agent for malaria infection, wherein the cytokine production level in the case of administering a test substance and hemozoin, synthetic hemozoin or derivatives thereof to MyD88+/+ and TLR9+/+ nonhuman animals and the cytokine production level in the case of administering a test substance and hemozoin, synthetic hemozoin or derivatives thereof to MyD88−/− and/or TLR9 1/− nonhuman animal, are measured and evaluated; a method for screening a preventative or therapeutic agent for malaria infection, wherein the cytokine production level in cells in the case of administering a test substance and hemozoin, synthetic hemozoin or derivatives thereof to MyD88+/+ and TLR9+/+ gene-expressing cells and the cytokine production level in cells in the case of administering a test substance and hemozoin, synthetic hemozoin or derivatives thereof to MyD88−/− and/or TLR9−/− gene-expressing cells, are compared and evaluated; and a method for elucidating a mechanism of immune-response induction through the TLR9-MyD88-dependent pathway.

The instant invention still further relates to a TLR9 agonist, a substance comprising hemozoin, synthetic hemozoin, or derivatives thereof as an active ingredient, and interacting with TLR9 to induce fully activated intracellular signaling. The TLR9 agonist is capable of activating MyD88; inducing immune responses involving the production and the like of any one or more cytokines selected from TNF-α, IL-12p40, MCP-1, IL-6, and IFNα through the TLR-MyD88 dependent pathway; and selectively activating TLR9 without activating TLR2, TLR4, TLR7, or TRIF, and thus the TLR9 agonist can be used as an agent for regulating innate immunity.

The instant invention furthermore relates to a method for using hemozoin, synthetic hemozoin, or derivatives thereof as a ligand for TLR9. Such method includes a method for inducing immune responses involving the production and the like of any one or more cytokines selected from TNF-α, IL-12p40, MCP-1, IL-6, and IFNα through the TLR9-MyD88 dependent pathway; and a method for controlling innate immunity. Specific aspects of such methods include the methods exemplified above as specific aspects of a method for using the instant invention.

The instant invention will be described more specifically with reference to the following examples, while the technical scope of the instant invention will not be limited to these exemplifications.

EXAMPLE 1

(Activation of Innate Immune Activity by HZ and the Regulation Thereof)
(Materials and Methods)
(Mice)

Mutant mice (MyD88-, TRIF-, TLR2-, TLR4-, TLR7-, and TLR9-deficient mice) either on a 129/Ola×C57/BL6 or C57/BL6 background were generated as described in literatures (Immunity 9: 143-150, 1999; Immunity 11: 443-451, 1999; Nature 408: 740-745, 2000; Nat. Immunol. 3: 196-200, 2002; Science 301: 640-643, 2003). Age-matched groups of wild type mice and mutant mice were used for experiments. For in-vivo studies, 1500 μg HZ purified from *P. falciparum* culture and synthetic HZ (β-hematin) were injected intraperitoneally into wild-type mice, MyD88−/− mice, or TLR9−/− mice (J. Immunol. 172: 3101-3110, 2004). Sera were collected from tails at 1, 2, 4, and 6 hours for cytokine ELISA.

(Reagents)

Synthetic CpG oligodeoxynucleotides (ODN) D35 were synthesized and purchased from Hokkaido System Science Co., Ltd. Lipopolysaccharides (LPS) from Salmonella minnesota Re-595, hemin chloride, and chloroquine (CQ) were purchased from Sigma-Aldrich. DNase (DNase-I) was purchased from Invitrogen.

(Preparation of HZ and Synthetic HZ (β-hematin))

HZ (nonsoluble crystalloid structure) was purified from red blood cells infected with *P. falciparum* (3D7 strain) (Infect. Immun. 70: 3939-3943, 2002; Proc. Natl. Acad. Sci. U.S.A 93: 11865-11870, 1996; Proc. Natl. Acad. Sci. U.S.A 88: 325-329, 1991). In brief, after saponin lysis of red blood cells, parasites were sonicated and washed seven to eight times in 2% dodecyl sodium sulfate (SDS). Then the pellets were incubated with Proteinase K (2 mg/ml) at 37° C. overnight. The pellets were then washed three times in 2% SDS and incubated in 6 M urea for 3 hours at room temperature on a shaker. After three to five washes in 2% SDS and then in distilled water, the HZ pellets were resuspended in distilled water, and sonicated again before use. In some experiments, as described in a literature (J. Immunol. 167: 2602-2607, 2001), HZ was either heat inactivated at 95° C. for 15 minutes or treated with 100 U/ml DNase-I for 1 hour. The DNase-I treatment was performed by removing genomic DNA completely from *P. falciparum* crude extract (FIGS. 5a-5b).

Quantification of nucleic acid and protein was performed by using a spectrophotometer or by ethidium bromide staining in agarose gel, BCA method (Biorad), or the pyrogallol red method (Wako Pure Chemical Industries, Ltd.). Total lipid (TP) was measured by TLC (thin-layer chromatography) using Bligh-Dyer method (Toray Research Center) or by an enzymatic method using the Iatron LQ (Mitsubishi Kagaku Iatron, Inc.). Synthetic HZ (β-hematin) was purified using the protocol of Jaramillo et al. (J. Immunol. 172: 3101-3110) based on acetic acid treatment and alkaline bicarbonate wash. To avoid endotoxin contaminations, all solutions were prepared using endotoxin-free PBS or distilled water. Endotoxin levels measured by LAL assays (Bio-Whittaker) were less than 0.001 EU for each nmole HZ used.

(Quantification of HZ or Synthetic HZ (β-hematin))

The concentration of HZ or synthetic HZ was determined by depolymerizing heme polymers in 20 mM sodium hydroxide/2% SDS solution for 2 hours at room temperature. The O.D. was read at 400 nm (Proc. Natl. Acad. Sci. U.S.A 93: 11865-11870, 1996). The molar extinction coefficient for heme is $1\times10^5$ at 400 nm, and 25 μg *P. falciparum* HZ is equal to 29 nmole of heme content.

(Cells)

Single cell suspensions of spleen cells ($5\times10^5$ cells/well) were cultured in complete RPMI 1640 medium supplemented with 10% FCS for 48 hours. Flt3 ligand-induced bone marrow-derived DCs (FL-DCs) ($1\times10^5$ cells/well) were generated by culturing bone marrow cells with Flt3 ligand (100 ng/ml; Pepro Tech) for eight to nine days in DMEM medium containing 10% FCS. The cells were stimulated in the presence of the indicated stimuli and supernatants were collected for cytokine ELISA.

(Cytokine ELISA)

Murine TNF-α, IL-12p40, MCP-1, IL-6 (R & D Systems), and IFNα (PBL Bio. Lab) were measured either from the supernatants or the sera by ELISA according to the manufacturer's instructions.

(Flow Cytometric Analysis of Costimulatory Molecule Expressions)

Cell surface molecule expressions of the stimulated cells were measured as described in a literature (J. Exp. Med. 196: 269-274, 2002). In brief, the stimulated cells were washed in cooled PBS, fixed, and stained with FITC-labeled antibody, PE-labeled antibody, Cy-Chrome-labeled antibody, and APC-labeled antibody, in the presence of anti-CD 16 antibody for 30 minutes at room temperature. The stained cells were washed, re-suspended in PBS/0.1% BSA/0.1% NaN3, and analyzed by FACSCaliber followed by analysis using CellQuest software (BD). All antibodies were obtained from BD.

(Statistical Analysis)

Statistically significant differences were analyzed using Student's t-test. $P<0.05$ was considered significant.

(Test, Results, and Evaluations)
(Activation of Murine Spleen Cells and Dentritic Cells Though the MyD88-Dependent Pathway by Purified HZ from *P. falciparum*)

To examine whether purified HZ from *P. falciparum* activates the murine immune system, spleen cells and DCs (murine myeloid dendritic cells) were stimulated in vitro with purified HZ and proinflammatory cytokine production in the culture supernatant was measured by ELISA. FL-DCs (Flt3 ligand-induced bone marrow-derived DCs) produced large amounts of TNFα, IL-12p40, monocyte chemoattractant factor-1 (MCP-1), and IL-6, in response to HZ in a dose-dependent manner to a similar extent to that of CpG ODN (FIG. 1a). To examine the roles of TLRs in HZ-induced innate immune activation, mice lacking MyD88, an essential adaptor molecule for cytokine inductions mediated by many TLRs, were used (Nat. Rev. Immunol. 4: 499-511, 2004). FL-DCs from MyD88−/− mice showed significantly impaired levels of TNFα, IL-12p40, MCP-1, and IL-6 productions upon stimulation with HZ (FIG. 1b).

Similarly, MyD88−/− spleen cells showed impaired responses to produce MCP-1, IL-6, TNFα, IL-12p40, and INF-inducible protein 10 (IP-10) in response to HZ (FIG. 1c). Additionally, hemozoin stimulated both CD11c+, B220+plasmacytoid DC subset and CD11c+, B220—myeloid DC subset of FL-DCs to up-regulate the expressions of CD40 and CD86 that were inhibited in both FL-DC subsets in MyD88−/− mice (FIG. 1d).

(TRIF-dependency of HZ activation of innate immune responses)

To confirm that HZ-induced innate immune activation is solely dependent on MyD88, mice lacking TRIF (Toll/IL-1 receptor (TIR)-region-containing adaptor), an essential adaptor molecule for the MyD88-independent pathway, were used (Nat. Rev. Immunol. 4: 499-511, 2004). In contrast to MyD88-/- mice, FL-DCs from TRIF-/- mice responded to HZ and produced TNFα and IL-12p40 (p<0.05, TRIF-/- vs. media) comparable to the value of wild type mice (p>0.05) (FIG. 2). LPS-induced TNFα and IL-12p40 were impaired in FL-DCs of TRIF-/- mice, suggesting that a large amount of HZ purified from *P. falciparum* cultures was not contaminated with LPS. These data demonstrated that HZ activates a proinflammatory response in mice through MyD88 and that one of the MyD88-dependent TLRs is involved in the recognition of HZ.

(TLR-9-Dependency of HZ Activation of Innate Immune Responses)

Further experiments were performed using spleen cells and DCs obtained from TLR2-/- mice, TLR4-/- mice, TLR7-/- mice, and TLR9-/- mice to examine whether HZ-induced innate immune activation was impaired or altered. HZ stimulated FL-DCs in wild type mice, TLR2-/- mice, TLR4-/- mice, and TLR7-/- mice to up-regulate CD40 and CD86 both in CD11c+, B220+plasmacytoid DC subset and CD11c+, B220-myeloid DC subset (FIGS. 3a-1 to 3a-2). In contrast, both FL-DC subsets derived from TLR9-/- mice failed to up-regulate CD40 and CD86 in response to HZ (FIGS. 3a-1 to 3a-2).

Similarly, FL-DCs derived from wild type mice, TLR2-/- mice, TLR4-/- mice, and TLR7-/- mice, but not from TLR9-/- mice, produced TNFα, IL-12p40, MCP-1, and IL-6 in response to HZ (FIG. 3b). It is of note that HZ did not induce IFNα by FL-DCs, suggesting that the HZ-induced cytokine profile is similar to that of K-type CpGODN (also known as B-type), but distinct from that of D-type ODN (also know as A-type) or known natural DNA ligands for TLR9 such as bacterial DNA, viral DNA (FIG. 3c) (Nat. Rev. Immunol. 4: 249-258, 2004). Nevertheless, these data clearly demonstrate that TLR9 and MyD88 are critical for HZ-induced activation in murine spleen cells and DCs.

(In vivo MyD88/TLR9 dependency of HZ activation of proinflammatory cytokines)

Figure 4A:
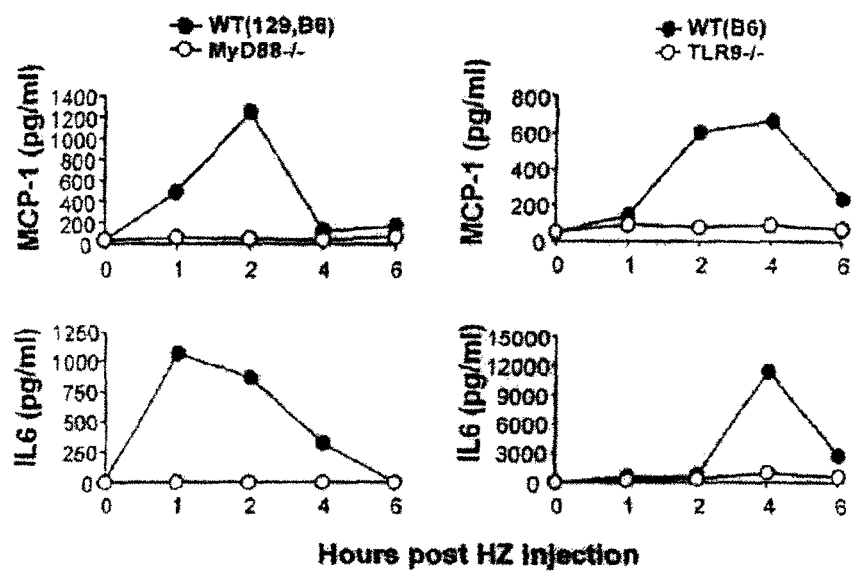
FIGS. 4a to 4b are a series of figures showing the results of the measurement of IL-6 and MCP-1 production levels in the sera by ELISA, after injecting synthetic HZ to wild type mice or TLR9−/− mice to study whether synthetic HZ activates the innate immune system in a TLR9-dependent manner in an example of the instant invention.

To confirm that HZ activation is mediated by TLR9 and dependent on MyD88 in vivo, purified *P. falciparum* HZ was injected intraperitoneally into wild type mice and MyD88-/- mice or TLR9-/- mice, and the serum cytokine production levels were monitored. The HZ injection significantly increased serum levels of MCP-1 and IL-6 in wild type mice, which peaked between 1 and 4 hours and declined within 6 hours (FIG. 4a). In contrast, such increases were completely inhibited in MyD88-/- mice and TLR9-/- mice. After 6 hours, the cytokine levels declined in wild type mice. These data clearly demonstrate that HZ-induced proinflammatory responses were mediated by TLR9 and MyD88 both in vitro and in vivo.

Figure 4B:
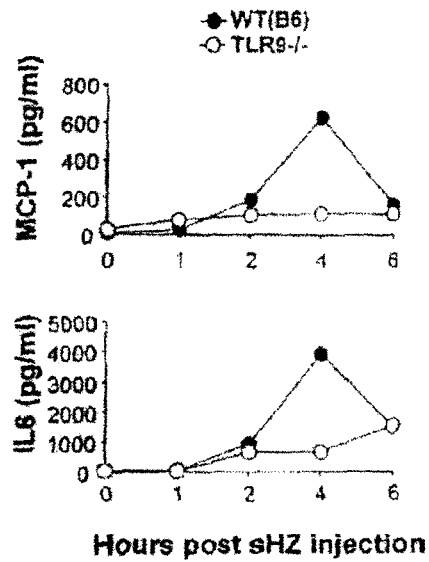

Synthetic HZ (β-hematin, synthesized from monomeric heme in laboratory conditions) is structurally similar to HZ formed naturally by parasites (Proc. Natl. Acad. Sci. U.S.A 93: 11865-11870, 1996; Proc. Natl. Acad. Sci. U.S.A 88: 325-329, 1991), and is free of contaminant derived from parasites or cultures. To examine whether synthetic HZ activates the innate immune system in a TLR9-dependent manner, synthetic HZ was injected into wild-type mice or TLR9-/- mice, and then IL-6 and MCP-1 production levels in sera were monitored. Synthetic HZ injection into wild type mice induced the productions of MCP-1 and IL-6 in sera, which peaked at 1-4 hours (FIG. 4b). In contrast, such responses were inhibited in TLR9-/- mice (FIG. 4b). These data suggest that synthetic HZ as well as natural HZ purified from *P. falciparum* stimulates the murine innate immune system, excluding the contribution of other possible contaminants to HZ-induced, TLR9-mediated innate immune activation.

To exclude any possible contaminants in or during HZ preparation from the *P. falciparum* culture a series of analyses was performed to determine the purity of HZ in addition to the extensive purification method described above (Infect. Immun. 70: 3939-3943, 2002). DNA or RNA was not detected in HZ or DNase-treated HZ solution (1 mM) either by ethidium bromide-stained agarose gel (FIG. 5a) or with a spectrophotometer. DNase treatment or heat-inactivation had no effect on HZ-induced TNFα and IL-12p40 productions by DCs (FIG. 5b). Further, genomic DNA and RNA isolated from *P. falciparum* did not activate innate immune responses significantly, including the productions of TNFα and IL-12 (unpublished experiment and (J. Immunol. 172: 3989-3993, 2004)). No protein or lipid was detected in the HZ solution (1 mM) by any method. Taken together, these data strongly suggest that HZ-induced, TLR9-mediated innate immune activation was not due to other contaminants.

(Chloroquine-Sensitivity of HZ-Induced Innate Immune Activation)

The anti-malarial formulation, chloroquine (CQ), has been reported to inhibit proinflammatory responses during malaria infection in addition to endosome/lysosome maturations and malarial hemozoin crystal formations, whereas the exact mechanism of anti-malarial effects of CQ is still under debate (Int. J. Parasitol. 32: 1645-1653, 2002; Life Sci. 74: 1957-1972, 2004). Recent evidence suggests that CQ also inhibits TLR9-mediated innate immune activation (J. Immunol. 160: 1122-1131, 1998). To examine the effect of CQ to HZ-induced proinflammatory responses, FL-DCs were stimulated with HZ in the presence of CQ. HZ-induced TNFα and IL-12p40 productions were diminished because of CQ (FIG. 5b).

These findings suggests that in addition to previously known mechanisms of CQ-inhibition of malaria pathogenesis, CQ may also inhibit HZ-induced, TLR9-mediated innate immune responses during malaria infection, possibly contributing to its therapeutic effects. Although further studies are needed, it is possible that in addition to its ability to inhibit HZ formation, CQ may also interfere with the interaction of HZ with TLR9 or inhibit the maturation of HZ-containing food vacuoles, thereby inhibiting the following innate immune activation.

It has been reported that TLR9 recognizes CpG motifs in microbial DNA or self-DNA-chromatin complex with specific IgG, whereas a non-DNA molecule as a TLR9 ligand has not been reported (Trends Immunol. 25: 381-386, 2004; Annu. Rev. Immunol. 20: 709-760, 2002). Recent study reported the first evidence of a non-DNA ligand recognized by TLR9. HZ is a crystal form of polymerized heme (ferriprotoporphyrin IX) produced in food vacuoles of parasites during the degradation of hemoglobin from red blood cells. Once captured by phagocytes such as macrophages and DCs, HZ accumulates in phagosomes where TLR9 can be recruited from endoplasmic reticulum via P13 kinase (J. Exp. Med. 196: 269-274, 2002; Nat. Immunol. 5: 190-198, 2004), suggesting that TLR9 can recognize HZ in phagosomes.

HZ is extremely hydrophobic, which may contribute to its immunostimulatory effect according to the hypothesis proposed recently (Nat. Rev. Immunol. 4: 469-478, 2004). It is of interest that HZ is originally derived from hemoglobin in the host red blood cells, but is modified by parasites from toxic heme into HZ, a metabolite which is nontoxic to parasites, so that the parasites may survive, which suggests that inert molecules (heme) become active "non-self" molecules in the innate immune system during malaria infection.

The biological role of HZ-induced, TLR9-mediated innate immune activation during malaria infection and of the host defense against such activation is currently under investigation. Preliminary results suggest that innate immune responses to malaria parasites are dependent on multiple factors in the host, including TLRs as well as and Plasmodium. Including the recent study, it is important to study whether TLR-mediated innate immune activation during malaria infection contributes to host protective immunity or to malarial immune escape mechanism. Further, it is also important to study the molecular mechanism by which TLR9 discriminates between CpGDNA and HZ. Nevertheless, observations to date clearly demonstrate that HZ, a heme metabolite during malaria infection, activates the innate immune system via TLR9-mediated, MyD88-dependent, and chloroquine-sensitive pathway, which may open a key to further understanding of malaria parasite-host interactions in innate immunity.

[Description of Drawings]

FIGS. 1a to 1d. Purified HZ from *P. falciparum* activates proinflammatory responses through the MyD88-dependent pathway: (a) FL-DCs from wild-type (WT) mice were stimulated with purified hemozoin (HZ) (30 μM and 100 μM) for 24 hours. TNFα, IL-12p40, MCP-1, or IL-6 production in the supernatant was measured by ELISA. As a control, 3 μM CpGDNA(D35) was used. (b) FL-DCs and (c) spleen cells of wild-type mice (solid bars) and of MyD88−/− mice (open bars) were stimulated with 30 μM HZ and CpGDNA (D35, 3 μM), or LPS (100 ng/ml) for 24 hours. The production of TNFα, IL-12p40, MCP-1, or IL-6 was measured by ELISA in the supernatant. (d) Myeloid DCs (CD11c+, B220−) and plasmacytoid DCs (CD11c+, B220+) were analyzed by flow-cytometry for CD40 and CD86 expressions. The shaded areas represent cells not stimulated by HZ, while solid lines represent cells stimulated by HZ. These results show the mean value +S.D. of duplicate cultures, and are representative of at least five independent experiments. "n.d." means "not detected".

FIG. 2. HZ-induced DC activation is TRIF-independent: FL-DCs from wild-type (WT) mice and TRIF−/− mice were incubated with 30 μM HZ and LPS (100 ng/ml) for 24 hours, after which supernatants were analyzed by ELISA to determine the production level of TNFα or IL-12p40. The results are the mean value +SEM for four independent experiments (n=4). P>0.05, HZ (WT) vs. HZ (TRI−/−). "n.d." means "not detected".

FIGS. 3a-1 to 3c. TLR9 mediates HZ-induced innate immune activation: (a) Myeloid DCs (CD11c+, B220−) and plasmacytoid DCs (CD11c+, B220+) from wild type (WT) mice and TLR2−/− mice, TLR4−/− mice, TLR7−/− mice, and TLR9−/− mice were analyzed by flow-cytometry to determine CD40 and CD88 expressions. The shaded areas represent cells not stimulated by HZ and the solid lines represent cells stimulated by HZ. Wild-type cells and TLR9−/−cells were incubated with the indicated stimuli and analyzed by ELISA for (b) TNFα, IL-12p40, MCP-1, or IL-6 production by spleen cells and for (c) TNFα production by FL-DCs. The results are representatives of at least five independent experiments. "n.d." means "not detected".

FIGS. 4a to 4b. Serum cytokine productions by HZ and synthetic HZ (β-hematin) in vivo are dependent on MyD88 and TLR9:

Either 1500 μg of (a) purified *P. falciparum* HZ or (b) synthetic HZ (sHZ) was intraperitoneally injected into MyD88−/− mice, TLR9−/− mice, or wild-type (WT) mice. Serum levels of MCP-1 and IL-6 were measured by ELISA at the indicated time points.

FIGS. 5a to 5b. Hemozoin is free of DNA, and HZ-induced proinflammatory cytokine production is DNase-resistant and heat-resistant, but chloroquine sensitive: (a) To detect DNA contamination, HZ was run on an agarose gel and stained with ethidium bromide. M, marker; lane 1, HZ solution (1 mM, 5 μl); lane 2, heat-inactivated HZ (1 mM, 5μl); lane 3, DNase-treated HZ (1 mM, 5 μl); lane 4, P. falciparum crude extract (5 μl from packed 100 ml of culture containing 4.5% parasitemia); DNase-treated crude extract (5 μl). (b) FL-DCs from C57/B6 mice were incubated either with 30 μM HZ or DNase treatment, heat-inactivation, and/or CQ (10 μM) for 24 hours. Then the supernatants were collected and measured for TNFα or IL-12p40 by ELISA. As a control, 3 μM CpGODN (D35) was used. The value of TNFα by D35 is shown in the figure. The results are representatives of one of three independent experiments performed in duplicate (mean +S.D.). *P.<0.05, HZ vs. HZ+CQ; **P.<0.05, CpGODN vs. CpGODN +CQ. "n.d." means "not detected".

INDUSTRIAL APPLICABILITY

In the instant invention, the inventors have elucidated the molecular level mechanism of immune responses in which HZ activates innate immunity in malaria parasites-host interactions. Based on this finding, in the instant invention, a method for detecting and measuring malaria infection that can be used for a diagnosis of malaria infection; and a method for screening a vaccine for malaria infection or a preventative or therapeutic agent for malaria infection using the method for detecting and measuring malaria infection by HZ induction were developed. Based on the above finding, a means for regulating HZ-induced, TLR9-mediated, and MyD88-dependent innate immune induction by using HZ, synthetic HZ, or derivatives thereof as an adjuvant or immunostimulant, was further developed.

By means of such developments, the instant invention presents measures to address a diagnosis of malaria infection; a creation of a vaccine or a preventative or therapeutic agent for malaria infection; and further, a regulation of innate immune induction as an immunotherapy for malaria infection, i.e., measures to address a diagnosis of malaria infection by targeting the innate-immune-related molecules including HZ, TLR9 (Toll-like receptor 9), and MyD88 or the signaling pathways thereof; and the development of an anti-malarial agent or an immunotherapy. Thus the instant invention can greatly contribute in these areas of applications. Further, CpGODN known as a TLR9 ligand has been developed as an innate-immune enhancer for combination therapy using CpGODN with a therapeutic agent for cancer or an infection; an anti-allergic agent; and a vaccine adjuvant. Therefore, hemozoin, synthetic hemozoin, or derivatives thereof can be developed in a similar manner as CpGODN as an innate-immune enhancer to be used with a therapeutic agent for cancer or for an infection in a combination therapy; an anti-allergic agent; and a vaccine adjuvant. Further, that hemozoin does not induce INFα in murine PDCs is an important finding for comparisons with various CpGODN activities.

The invention claimed is:

1. A method for stimulating innate immunity through the TLR9-MyD88-dependent pathway, comprising administering a composition consisting essentially of a TLR9 agonist to a subject under conditions that permit in vivo binding of the TLR agonist to a TLR9 protein,
   wherein the TLR9 agonist is hemozoin or β-hematin; and
   wherein the TLR9 protein consists of the amino acid sequence of SEQ ID NO: 2.

2. The method according to claim 1, wherein the TLR9 protein is encoded by (a) a DNA consisting of the nucleotide sequence shown by SEQ ID NO: 1 or (b) a DNA consisting of the complementary nucleotide sequence of SEQ ID NO: 1.

3. The method according to claim 1, wherein the administration of the composition causes the immune system to produce one or more cytokines selected from the group consisting of TNF-α, IL-12p40, MPC-1, IL-6, and IFNα.

* * * * *

SEQUENCE LISTING

<160> NUMBER OF SEQ ID NOS: 2

<210> SEQ ID NO 1
<211> LENGTH: 3257
<212> TYPE: DNA
<213> ORGANISM: Homo sapiens

<400> SEQUENCE: 1

| | | | | | |
|---|---|---|---|---|---|
| ccgctgctgc | ccctgtggga | agggacctcg | agtgtgaagc | atccttccct | gtagctgctg | 60 |
| tccagtctgc | ccgccagacc | ctctggagaa | gcccctgccc | ccagcatgg | gtttctgccg | 120 |
| cagcgccctg | cacccgctgt | ctctcctggt | gcaggccatc | atgctggcca | tgaccctggc | 180 |
| cctgggtacc | ttgcctgcct | tcctaccctg | tgagctccag | ccccacggcc | tggtgaactg | 240 |
| caactggctg | ttcctgaagt | ctgtgcccca | cttctccatg | gcagcacccc | gtggcaatgt | 300 |
| caccagcctt | tccttgtcct | ccaaccgcat | ccaccacctc | catgattctg | actttgccca | 360 |
| cctgcccagc | ctgcggcatc | tcaacctcaa | gtggaactgc | ccgccggttg | gcctcagccc | 420 |
| catgcacttc | ccctgccaca | tgaccatcga | gcccagcacc | ttcttggctg | tgcccaccct | 480 |
| ggaagagcta | aacctgagct | acaacaacat | catgactgtg | cctgcgctgc | ccaaatccct | 540 |
| catatccctg | tccctcagcc | ataccaacat | cctgatgcta | gactctgcca | gcctcgccgg | 600 |
| cctgcatgcc | ctgcgcttcc | tattcatgga | cggcaactgt | tattacaaga | cccctgcag | 660 |
| gcaggcactg | gaggtggccc | cgggtgccct | ccttggcctg | ggcaacctca | cccacctgtc | 720 |
| actcaagtac | aacaacctca | ctgtggtgcc | ccgcaacctg | ccttccagcc | tggagtatct | 780 |
| gctgttgtcc | tacaaccgca | tcgtcaaact | ggcgcctgag | gacctggcca | atctgaccgc | 840 |
| cctgcgtgtg | ctcgatgtgg | gcggaaattg | ccgccgctgc | gaccacgctc | caacccctg | 900 |
| catggagtgc | cctcgtcact | tccccagct | acatcccgat | accttcagcc | acctgagccg | 960 |
| tcttgaaggc | ctggtgttga | aggacagttc | tctctcctgg | ctgaatgcca | gttggttccg | 1020 |
| tgggctggga | aacctccgag | tgctggacct | gagtgagaac | ttcctctaca | aatgcatcac | 1080 |
| taaaaccaag | gccttccagg | gcctaacaca | gctgcgcaag | cttaacctgt | ccttcaatta | 1140 |
| ccaaaagagg | gtgtcctttg | cccacctgtc | tctggcccct | tccttcggga | gcctggtcgc | 1200 |
| cctgaaggag | ctggacatgc | acggcatctt | cttccgctca | ctcgatgaga | ccacgctccg | 1260 |
| gccactggcc | cgcctgccca | tgctccagac | tctgcgtctg | cagatgaact | tcatcaacca | 1320 |
| ggcccagctc | ggcatcttca | gggccttccc | tggcctgcgc | tacgtggacc | tgtcggacaa | 1380 |
| ccgcatcagc | ggagcttcgg | agctgacagc | caccatgggg | gaggcagatg | gagggagaa | 1440 |
| ggtctggctg | cagcctgggg | accttgctcc | ggccccagtg | gacactccca | gctctgaaga | 1500 |
| cttcaggccc | aactgcagca | ccctcaactt | caccttggat | ctgtcacgga | caacctggt | 1560 |
| gaccgtgcag | ccggagatgt | ttgcccagct | ctcgcacctg | cagtgcctgc | gcctgagcca | 1620 |
| caactgcatc | tcgcaggcag | tcaatggctc | ccagttcctg | ccgctgaccg | gtctgcaggt | 1680 |
| gctagacctg | tcccacaata | agctggacct | ctaccacgag | cactcattca | cggagctacc | 1740 |
| acgactggag | gccctggacc | tcagctacaa | cagccagccc | tttggcatgc | agggcgtggg | 1800 |
| ccacaacttc | agcttcgtgg | ctcacctgcg | caccctgcgc | cacctcagcc | tggcccacaa | 1860 |
| caacatccac | agccaagtgt | cccagcagct | ctgcagtacg | tcgctgcggg | ccctggactt | 1920 |
| cagcggcaat | gcactgggcc | atatgtgggc | cgagggagac | ctctatctgc | acttcttcca | 1980 |
| aggcctgagc | ggtttgatct | ggctggactt | gtccagaac | cgcctgcaca | ccctcctgcc | 2040 |
| ccaaacccctg | cgcaacctcc | ccaagagcct | acaggtgctg | cgtctccgtg | acaattacct | 2100 |

```
ggccttcttt aagtggtgga gcctccactt cctgcccaaa ctggaagtcc tcgacctggc    2160
aggaaaccag ctgaaggccc tgaccaatgg cagcctgcct gctggcaccc ggctccggag    2220
gctggatgtc agctgcaaca gcatcagctt cgtggccccc ggcttctttt ccaaggccaa    2280
ggagctgcga gagctcaacc ttagcgccaa cgccctcaag acagtggacc actcctggtt    2340
tgggcccctg gcgagtgccc tgcaaatact agatgtaagc gccaaccctc tgcactgcgc    2400
ctgtggggcg gcctttatgg acttcctgct ggaggtgcag gctgccgtgc ccggtctgcc    2460
cagccgggtg aagtgtggca gtccgggcca gctccagggc tcagcatct ttgcacagga    2520 cctgcgcctc tgcctggatg aggccctctc ctgggactgt ttcgccctct cgctgctggc    2580
tgtggctctg ggcctgggtg tgcccatgct gcatcacctc tgtggctggg acctctggta    2640
ctgcttccac ctgtgcctgg cctggcttcc ctggcgtggg cggcaaagtg ggcgagatga    2700
ggatgccctg ccctacgatg ccttcgtggt cttcgacaaa acgcagagcg cagtggcaga    2760
ctgggtgtac aacgagcttc gggggcagct ggaggagtgc cgtgggcgct ggcactccg    2820 cctgtgcctg gaggaacgcg actggctgcc tggcaaaacc ctctttgaga acctgtgggc    2880
ctcggtctat ggcagccgca agacgctgtt tgtgctggcc cacacggacc gggtcagtgg    2940
tctcttgcgc gccagcttcc tgctggccca gcagcgcctg ctggaggacc gcaaggacgt    3000
cgtggtgctg gtgatcctga gccctgacgg ccgccgctcc cgctacgtgc ggctgcgcca    3060
gcgcctctgc cgccagagtg tcctcctctg gccccaccag cccagtggtc agcgcagctt    3120
ctgggcccag ctgggcatgg ccctgaccag ggacaaccac cacttctata accggaactt    3180
ctgccaggga cccacggccg aatagccgtg agccggaatc ctgcacggtg ccacctccac    3240
actcacctca cctctgc                                                   3257
```

<210> SEQ ID NO 2
<211> LENGTH: 1032
<212> TYPE: PRT
<213> ORGANISM: Homo sapiens

<400> SEQUENCE: 2

```
Met Gly Phe Cys Arg Ser Ala Leu His Pro Leu Ser Leu Leu Val Gln
1               5                   10                  15

Ala Ile Met Leu Ala Met Thr Leu Ala Leu Gly Thr Leu Pro Ala Phe
            20                  25                  30

Leu Pro Cys Glu Leu Gln Pro His Gly Leu Val Asn Cys Asn Trp Leu
        35                  40                  45

Phe Leu Lys Ser Val Pro His Phe Ser Met Ala Ala Pro Arg Gly Asn
    50                  55                  60

Val Thr Ser Leu Ser Leu Ser Ser Asn Arg Ile His His Leu His Asp
65                  70                  75                  80

Ser Asp Phe Ala His Leu Pro Ser Leu Arg His Leu Asn Leu Lys Trp
                85                  90                  95

Asn Cys Pro Pro Val Gly Leu Ser Pro Met His Phe Pro Cys His Met
            100                 105                 110

Thr Ile Glu Pro Ser Thr Phe Leu Ala Val Pro Thr Leu Glu Glu Leu
        115                 120                 125

Asn Leu Ser Tyr Asn Asn Ile Met Thr Val Pro Ala Leu Pro Lys Ser
    130                 135                 140

Leu Ile Ser Leu Ser Leu Ser His Thr Asn Ile Leu Met Leu Asp Ser
145                 150                 155                 160
```

-continued

Ala Ser Leu Ala Gly Leu His Ala Leu Arg Phe Leu Phe Met Asp Gly
            165                 170                 175

Asn Cys Tyr Tyr Lys Asn Pro Cys Arg Gln Ala Leu Glu Val Ala Pro
            180                 185                 190

Gly Ala Leu Leu Gly Leu Gly Asn Leu Thr His Leu Ser Leu Lys Tyr
            195                 200                 205

Asn Asn Leu Thr Val Val Pro Arg Asn Leu Pro Ser Ser Leu Glu Tyr
    210                 215                 220

Leu Leu Leu Ser Tyr Asn Arg Ile Val Lys Leu Ala Pro Glu Asp Leu
225                 230                 235                 240

Ala Asn Leu Thr Ala Leu Arg Val Leu Asp Val Gly Gly Asn Cys Arg
            245                 250                 255

Arg Cys Asp His Ala Pro Asn Pro Cys Met Glu Cys Pro Arg His Phe
            260                 265                 270

Pro Gln Leu His Pro Asp Thr Phe Ser His Leu Ser Arg Leu Glu Gly
            275                 280                 285

Leu Val Leu Lys Asp Ser Ser Leu Ser Trp Leu Asn Ala Ser Trp Phe
            290                 295                 300

Arg Gly Leu Gly Asn Leu Arg Val Leu Asp Leu Ser Glu Asn Phe Leu
305                 310                 315                 320

Tyr Lys Cys Ile Thr Lys Thr Lys Ala Phe Gln Gly Leu Thr Gln Leu
                325                 330                 335

Arg Lys Leu Asn Leu Ser Phe Asn Tyr Gln Lys Arg Val Ser Phe Ala
            340                 345                 350

His Leu Ser Leu Ala Pro Ser Phe Gly Ser Leu Val Ala Leu Lys Glu
            355                 360                 365

Leu Asp Met His Gly Ile Phe Phe Arg Ser Leu Asp Glu Thr Thr Leu
    370                 375                 380

Arg Pro Leu Ala Arg Leu Pro Met Leu Gln Thr Leu Arg Leu Gln Met
385                 390                 395                 400

Asn Phe Ile Asn Gln Ala Gln Leu Gly Ile Phe Arg Ala Phe Pro Gly
                405                 410                 415

Leu Arg Tyr Val Asp Leu Ser Asp Asn Arg Ile Ser Gly Ala Ser Glu
            420                 425                 430

Leu Thr Ala Thr Met Gly Glu Ala Asp Gly Gly Glu Lys Val Trp Leu
            435                 440                 445

Gln Pro Gly Asp Leu Ala Pro Ala Pro Val Asp Thr Pro Ser Ser Glu
    450                 455                 460

Asp Phe Arg Pro Asn Cys Ser Thr Leu Asn Phe Thr Leu Asp Leu Ser
465                 470                 475                 480

Arg Asn Asn Leu Val Thr Val Gln Pro Glu Met Phe Ala Gln Leu Ser
            485                 490                 495

His Leu Gln Cys Leu Arg Leu Ser His Asn Cys Ile Ser Gln Ala Val
            500                 505                 510

Asn Gly Ser Gln Phe Leu Pro Leu Thr Gly Leu Gln Val Leu Asp Leu
            515                 520                 525

Ser His Asn Lys Leu Asp Leu Tyr His Glu His Ser Phe Thr Glu Leu
    530                 535                 540

Pro Arg Leu Glu Ala Leu Asp Leu Ser Tyr Asn Ser Gln Pro Phe Gly
545                 550                 555                 560

Met Gln Gly Val Gly His Asn Phe Ser Phe Val Ala His Leu Arg Thr
                565                 570                 575

Leu Arg His Leu Ser Leu Ala His Asn Asn Ile His Ser Gln Val Ser

-continued

```
            580             585             590
Gln Gln Leu Cys Ser Thr Ser Leu Arg Ala Leu Asp Phe Ser Gly Asn
            595             600             605
Ala Leu Gly His Met Trp Ala Glu Gly Asp Leu Tyr Leu His Phe Phe
            610             615             620
Gln Gly Leu Ser Gly Leu Ile Trp Leu Asp Leu Ser Gln Asn Arg Leu
625             630             635             640
His Thr Leu Leu Pro Gln Thr Leu Arg Asn Leu Pro Lys Ser Leu Gln
            645             650             655
Val Leu Arg Leu Arg Asp Asn Tyr Leu Ala Phe Phe Lys Trp Trp Ser
            660             665             670
Leu His Phe Leu Pro Lys Leu Glu Val Leu Asp Leu Ala Gly Asn Gln
            675             680             685
Leu Lys Ala Leu Thr Asn Gly Ser Leu Pro Ala Gly Thr Arg Leu Arg
            690             695             700
Arg Leu Asp Val Ser Cys Asn Ser Ile Ser Phe Val Ala Pro Gly Phe
705             710             715             720
Phe Ser Lys Ala Lys Glu Leu Arg Glu Leu Asn Leu Ser Ala Asn Ala
            725             730             735
Leu Lys Thr Val Asp His Ser Trp Phe Gly Pro Leu Ala Ser Ala Leu
            740             745             750
Gln Ile Leu Asp Val Ser Ala Asn Pro Leu His Cys Ala Cys Gly Ala
            755             760             765
Ala Phe Met Asp Phe Leu Leu Glu Val Gln Ala Val Pro Gly Leu
            770             775             780
Pro Ser Arg Val Lys Cys Gly Ser Pro Gly Gln Leu Gln Gly Leu Ser
785             790             795             800
Ile Phe Ala Gln Asp Leu Arg Leu Cys Leu Asp Glu Ala Leu Ser Trp
            805             810             815
Asp Cys Phe Ala Leu Ser Leu Leu Ala Val Ala Leu Gly Leu Gly Val
            820             825             830
Pro Met Leu His His Leu Cys Gly Trp Asp Leu Trp Tyr Cys Phe His
            835             840             845
Leu Cys Leu Ala Trp Leu Pro Trp Arg Gly Arg Gln Ser Gly Arg Asp
            850             855             860
Glu Asp Ala Leu Pro Tyr Asp Ala Phe Val Val Phe Asp Lys Thr Gln
865             870             875             880
Ser Ala Val Ala Asp Trp Val Tyr Asn Glu Leu Arg Gly Gln Leu Glu
            885             890             895
Glu Cys Arg Gly Arg Trp Ala Leu Arg Leu Cys Leu Glu Glu Arg Asp
            900             905             910
Trp Leu Pro Gly Lys Thr Leu Phe Glu Asn Leu Trp Ala Ser Val Tyr
            915             920             925
Gly Ser Arg Lys Thr Leu Phe Val Leu Ala His Thr Asp Arg Val Ser
            930             935             940
Gly Leu Leu Arg Ala Ser Phe Leu Leu Ala Gln Gln Arg Leu Leu Glu
945             950             955             960
Asp Arg Lys Asp Val Val Val Leu Val Ile Leu Ser Pro Asp Gly Arg
            965             970             975
Arg Ser Arg Tyr Val Arg Leu Arg Gln Arg Leu Cys Arg Gln Ser Val
            980             985             990
Leu Leu Trp Pro His Gln Pro Ser Gly Gln Arg Ser Phe Trp Ala Gln
            995             1000            1005
```

-continued

```
Leu Gly Met Ala Leu Thr Arg Asp Asn His His Phe Tyr Asn Arg
    1010            1015            1020

Asn Phe Cys Gln Gly Pro Thr Ala Glu
    1025            1030
```